US012746386B2

(12) United States Patent
Baker et al.

(10) Patent No.: US 12,746,386 B2
(45) Date of Patent: Sep. 29, 2026

(54) INTEGRATED CONDUCTOR COIL ELECTRODE

(71) Applicant: Medtronic, Inc., Minneapolis, MN (US)

(72) Inventors: Paul D. Baker, Oakdale, MN (US); Mark T. Marshall, Cape Coral, FL (US); Jonathan A. Hughes, Blaine, MN (US); Kevin R. Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 732 days.

(21) Appl. No.: 17/938,661

(22) Filed: Oct. 6, 2022

(65) Prior Publication Data

US 2024/0115852 A1 Apr. 11, 2024

(51) Int. Cl.
*A61N 1/05* (2006.01)

(52) U.S. Cl.
CPC .................................... *A61N 1/05* (2013.01)

(58) Field of Classification Search
CPC ........... A61N 1/05; A61N 1/057; A61N 1/056
See application file for complete search history.

(56) References Cited

U.S. PATENT DOCUMENTS

| | | | | |
|---|---|---|---|---|
| 4,595,012 | A * | 6/1986 | Webler | A61N 1/056 600/374 |
| 4,922,927 | A | 5/1990 | Fine et al. | |
| 5,534,022 | A | 7/1996 | Hoffmann et al. | |
| 8,335,572 | B2 | 12/2012 | Ameri | |
| 8,738,150 | B2 | 5/2014 | Li et al. | |
| 9,220,913 | B2 | 12/2015 | Christie et al. | |
| 9,446,232 | B2 | 9/2016 | Duncan et al. | |
| 9,855,419 | B2 | 1/2018 | Laske et al. | |
| 10,786,679 | B2 | 9/2020 | Reddy et al. | |
| 11,235,145 | B2 | 2/2022 | Foster et al. | |

(Continued)

FOREIGN PATENT DOCUMENTS

| | | | |
|---|---|---|---|
| WO | 2020263615 | A1 | 12/2020 |
| WO | 2021148954 | A1 | 7/2021 |

OTHER PUBLICATIONS

Jang, Hansaem et al.; "Iridium oxide fabrication and application: A review;" Journal of Energy Chemistry, vol. 46, Jul. 2020, pp. 152-172 (Year: 2020).*

(Continued)

*Primary Examiner* — Lynsey C Eiseman
*Assistant Examiner* — Christopher J Mutchler
(74) *Attorney, Agent, or Firm* — Shumaker & Sieffert, P.A.

(57) ABSTRACT

An implantable medical lead includes a lead body extending from a proximal end to a distal end. The lead body includes an inner insulation layer and an outer insulation layer. The lead further includes a sleeve mechanically supported by the lead body at the distal end of the lead body. The lead further includes an uninsulated conductor coil. The uninsulated conductor coil includes a first portion having a first inner diameter, and a second portion having a second inner diameter and extending distally from the outer insulation layer. The first portion is positioned between the inner insulation layer and the outer insulation layer. The second inner diameter is greater than the first inner diameter. An outer surface of the second portion is exposed.

20 Claims, 4 Drawing Sheets

(56) References Cited

U.S. PATENT DOCUMENTS

| | | | | |
|---|---|---|---|---|
| 11,253,699 | B1 | 2/2022 | Williams et al. | |
| 2002/0049485 | A1* | 4/2002 | Smits | A61N 1/056 607/122 |
| 2004/0054390 | A1* | 3/2004 | Zarembo | A61N 1/056 607/122 |
| 2004/0064172 | A1 | 4/2004 | McVenes et al. | |
| 2004/0176782 | A1* | 9/2004 | Hanse | A61N 1/057 606/129 |
| 2006/0095107 | A1 | 5/2006 | Osypka | |
| 2008/0294229 | A1 | 11/2008 | Friedman et al. | |

OTHER PUBLICATIONS

International Search Report and Written Opinion of International Application No. PCT/IB2023/059273 dated Nov. 23, 2023, 10 pp.

* cited by examiner

INTEGRATED CONDUCTOR COIL ELECTRODE

TECHNICAL FIELD

This disclosure relates generally to implantable medical devices and, more particularly, to implantable medical leads.

BACKGROUND

Some types of implantable medical devices, such as cardiac pacemakers or implantable cardioverter defibrillators, provide electrical therapy to a heart of a patient via electrodes. The electrical therapy may be delivered to the heart for pacing, cardioversion or defibrillation. The implantable medical device may include electronic circuitry to deliver the electrical therapy, where the electronic circuitry is encapsulated by a housing, such as a metal, e.g., titanium housing.

In some examples, the implantable medical devices may provide electrical therapy via implantable medical leads that include one or more electrodes. Implantable medical leads may be adapted to treat a wide variety of cardiac dysfunctions. An implantable medical lead may be navigated through vasculature of a patient to reach one or more target locations for sensing and/or therapy delivery. An electrode supported by the implantable medical lead may establish electrical communication with tissues of the heart to sense cardiac signals generated by the heart and/or deliver cardiac pacing to the patient.

SUMMARY

In some examples, an implantable medical lead comprises: a lead body extending from a proximal end to a distal end, the lead body comprising: an inner insulation layer defining an inner insulation layer lumen; and an outer insulation layer; a sleeve mechanically supported by the lead body at the distal end of the lead body; and an uninsulated conductor coil electrically connected to an implantable medical device, the uninsulated conductor coil comprising: a first portion having a first inner diameter, wherein the first portion is positioned between the inner insulation layer and the outer insulation layer; and a second portion extending distally from the outer insulation layer, the second portion having a second inner diameter sized to receive the sleeve, wherein the second inner diameter is greater than the first inner diameter, and wherein an outer surface of the second portion is exposed.

In some examples, a system comprises: an implantable medical device; an implantable medical lead comprising: a lead body extending from a proximal end to a distal end, the lead body comprising: an inner insulation layer defining an inner insulation layer lumen; and an outer insulation layer; a sleeve mechanically supported by the lead body at the distal end of the lead body; and an uninsulated conductor coil electrically connected to the implantable medical device, the uninsulated conductor coil comprising: a first portion having a first inner diameter, wherein the first portion is positioned between the inner insulation layer and the outer insulation layer; and a second portion extending distally from the outer insulation layer, the second portion having a second inner diameter sized to receive the sleeve.

In some examples, a method of manufacturing an implantable medical lead comprises: forming a sleeve of the implantable medical lead, wherein the sleeve comprises a distal electrode; electrically connecting an inner conductor coil to the distal electrode; forming an inner insulation layer that covers the inner coil; forming an uninsulated conductor coil defining a coil lumen, wherein the uninsulated conductor coil comprises: a first portion having a first inner diameter; and a second portion having a second inner diameter sized to receive the sleeve, wherein the second inner diameter is greater than the first inner diameter; positioning at least a part of the inner insulation layer within the coil lumen; connecting the second portion to the sleeve; and forming an outer insulation layer that covers the first portion of the uninsulated conductor coil without covering the second portion of the uninsulated conductor coil such that the second portion remains exposed.

The details of one or more examples are set forth in the accompanying drawings and the description below. Other features, objects, and advantages will be apparent from the description and drawings, and from the claims.

DETAILED DESCRIPTION

A medical system may be temporarily implanted in a patient and then removed. For example, a temporary medical system may be configured to assist with cardiac pacing for up to 7 days and then removed. Such a system may include a temporary implantable medical device (IMD) and a temporary implantable medical lead.

In general, an IMD may include components capable of coupling electrodes of an implantable medical lead to circuitry of the IMD. For example, the electrodes may be coupled to electrical conductors within the lead body, which in turn may be connected to therapy circuitry and/or sensing circuitry of the IMD. However, conventional manufacturing techniques for chronically implanted leads may not be cost-effective for a temporary medical lead. For example, the electrodes may be formed from more expensive materials (e.g., solid metal tubes) that require extensive processing. Additionally, the electrodes may need to be connected to electrical conductors, increasing manufacturing costs.

In accordance with techniques of this disclosure, an implantable medical lead may include an uninsulated conductor coil electrically connected to an IMD. The uninsulated conductor coil, which may be formed from a conductive material, such as multiphase nickel (e.g., MP35N), may be connected to circuitry of the IMD. Additionally, a portion of the uninsulated conductor coil may be exposed to tissue of a patient such that the exposed portion of the uninsulated conductor coil may operate as an electrode. In this way, the electrical conductor and electrode of a lead may be integrated into a single component. Thus, the techniques of this disclosure may eliminate costs associated with using more expensive materials, metal ring components, joining processes, etc.

Although primarily described herein with respect to cardiac electric therapy, IMDs and implantable medical leads as described herein may be configured to deliver electrical therapy other than cardiac electric therapy. Furthermore, although primarily described herein as being an implantable medical lead (e.g., a cardiac lead), the techniques may also be applied to another type of device, such as a catheter.

Figure 1:
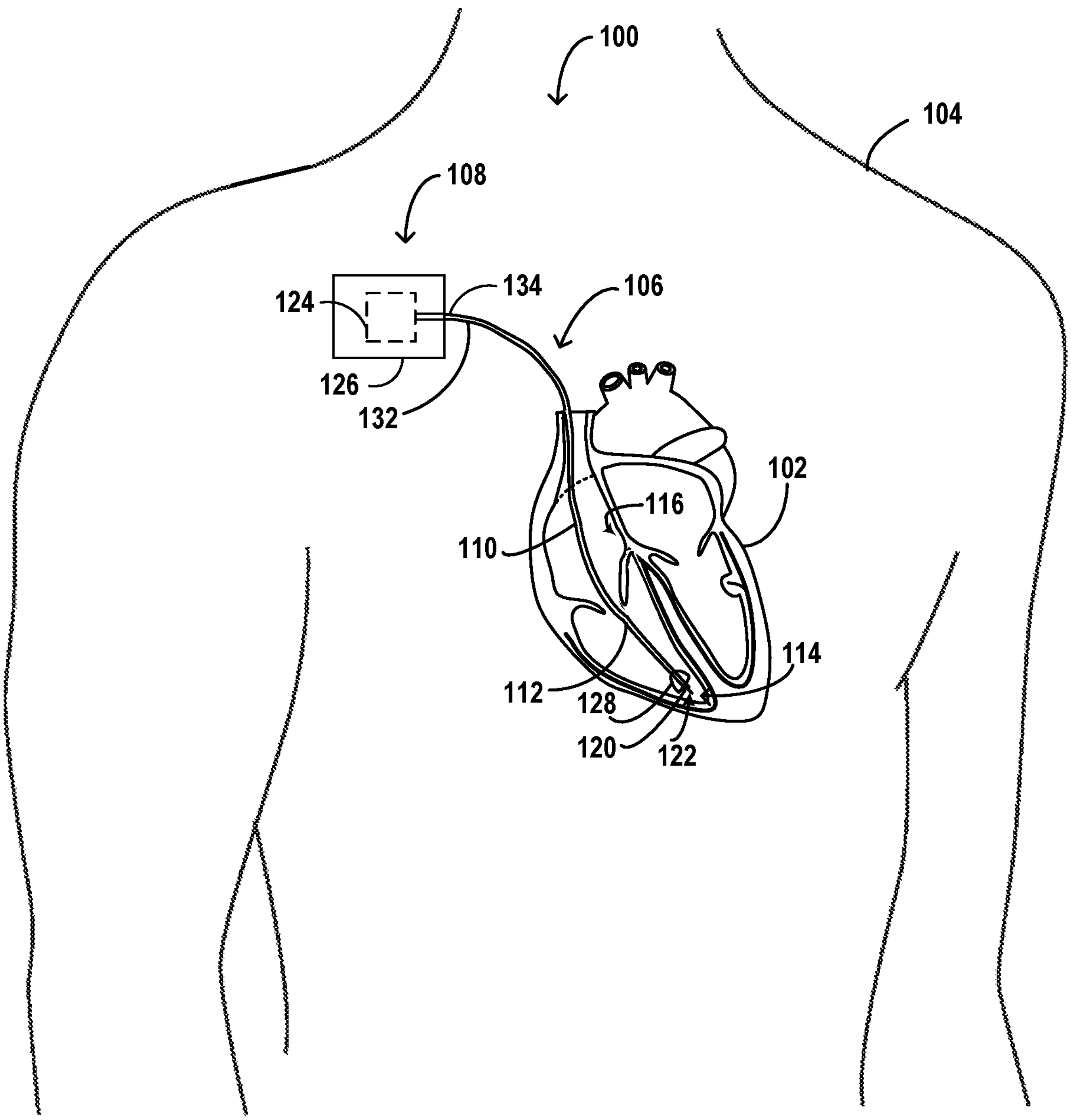
FIG. 1 is a conceptual diagram illustrating an example implantable medical system in accordance with techniques of this disclosure.

FIG. 1 is a conceptual diagram illustrating an example implantable medical system 100 ("system 100") configured to deliver therapy (e.g., pacing) to a heart 102 of a patient 104. System 100 includes an implantable medical lead 106 ("lead 106") extending from an implantable medical device 108 ("medical device 108") through vasculature of patient 104. Lead 106 includes a lead body 110 with a distal portion 112 of lead body 110 ("lead body distal portion 112") generally positioned at a target site 114 within patient 104. In examples, as illustrated in FIG. 1, target site 114 may be a region in the right ventricular apex of heart 102. In examples, lead 106 may be oriented such that lead body distal portion 112 positions at another portion of heart 102. For example, lead 106 may be oriented such that lead body distal portion 112 generally positions at a target site 116 in the atrioventricular septal wall. System 100 may include additional leads coupled to medical device 108 and extending into heart 102.

Lead body distal portion 112 may include a distal end 120 ("lead body distal end 120"). In some examples, lead body distal portion 112 may mechanically support a fixation member 122 configured to extend distally beyond lead body distal end 120. Fixation member 122 may be configured to penetrate tissue of the patient 104 at or near target sites, such as target sites 114, 116. Fixation member 122 may have various shapes such as helices, tines, screws, rings, and so on.

In some examples, fixation member 122 may mechanically support a distal electrode (not shown) configured to electrically communicate with tissue when fixation member 122 positions the distal electrode in proximity to target sites 114, 116. In some examples, fixation member, or a portion thereof, may operate as the distal electrode. In some examples, the distal electrode may be configured to provide pacing to heart 102. The distal electrode may be electrically connected to one or more conductors extending through lead body 110. Circuitry 124 configured to deliver therapy signals to and/or sense cardiac signals from the distal electrode using the conductor. Fixation member 122 may be configured to position the distal electrode such that the distal electrode conducts the electrical signals to the target tissue of heart 102, causing the cardiac muscle, e.g., of the ventricles, to depolarize and, in turn, contract at a regular interval.

System 100 may include a balloon 128 located at lead body distal portion 112. Balloon 128 may define an interior volume configured to receive an inflating medium (e.g., air, saline, or another medium), in turn resulting in inflation of balloon 128. In examples, lead body 110 defines an inflation lumen (not shown) fluidly coupled to the interior volume and configured such that a clinician may deliver the inflating medium to the interior volume defined by balloon 128. The inflation lumen may extend from lead body distal portion 112 to a proximal portion 132 of lead body 110 ("lead body proximal portion 132"). An exterior surface of lead body proximal portion 132 at or near a proximal end 134 of lead body 110 ("lead body proximal end 134") may define an opening to the inflation lumen.

Balloon 128 in the inflated configuration may substantially surround a portion of fixation member 122 to maintain at least a radial displacement between fixation member 122 and anatomical structures within patient 104 during the transit of lead body distal portion 112. System 100 may be configured to accommodate other pathways or techniques to reach target sites within patient 104 with balloon 128 in the inflated configuration. For example, system 100 may be configured such that balloon 128 in the inflated configuration accommodates transit through an innominate vein, an interior vena cava (IVC), and/or another veinous pathway enroute to a chamber of heart 102.

Lead 106 may include a proximal electrode (e.g., an electrode proximal of a distal electrode positioned at or near lead body distal portion 112). In examples where the proximal electrode is a discrete electrode (e.g., a separate component, such as a ring electrode), the proximal electrode may need to be electrically connected to a conductor. However, conventional techniques for manufacturing and connecting discrete electrodes and conductors may not be cost-effective for a temporary medical lead (e.g., due to types of materials, additional processing steps, etc.).

In accordance with techniques of this disclosure, lead 106 may include an uninsulated conductor coil electrically connected to IMD 108. The uninsulated conductor coil may be electrically connected to circuitry 124. Additionally, a portion of the uninsulated conductor coil may be exposed to tissue of patient 104 such that the uninsulated conductor coil may operate as an electrode. In this way, a conductor and an electrode of a lead may be integrated into a single component—i.e., the uninsulated conductor coil. Thus, the techniques of this disclosure may eliminate costs associated with using more expensive materials, metal ring components, joining processes, etc.

As used herein, a conductor coil is distinguishable from a conductor cable in that a conductor coil is a structure formed or arranged in a shape of a spiral and defining a lumen, whereas a conductor cable includes a plurality of wires twisted around a central core. A conductor coil may be relatively rigid and able to maintain a coiled shape without assistance. Conversely, a conductor cable may be relatively flexible and require, for example, an insulation layer to at least partially surround the conductor cable to prevent uncoiling of the conductor cable.

Figure 2:
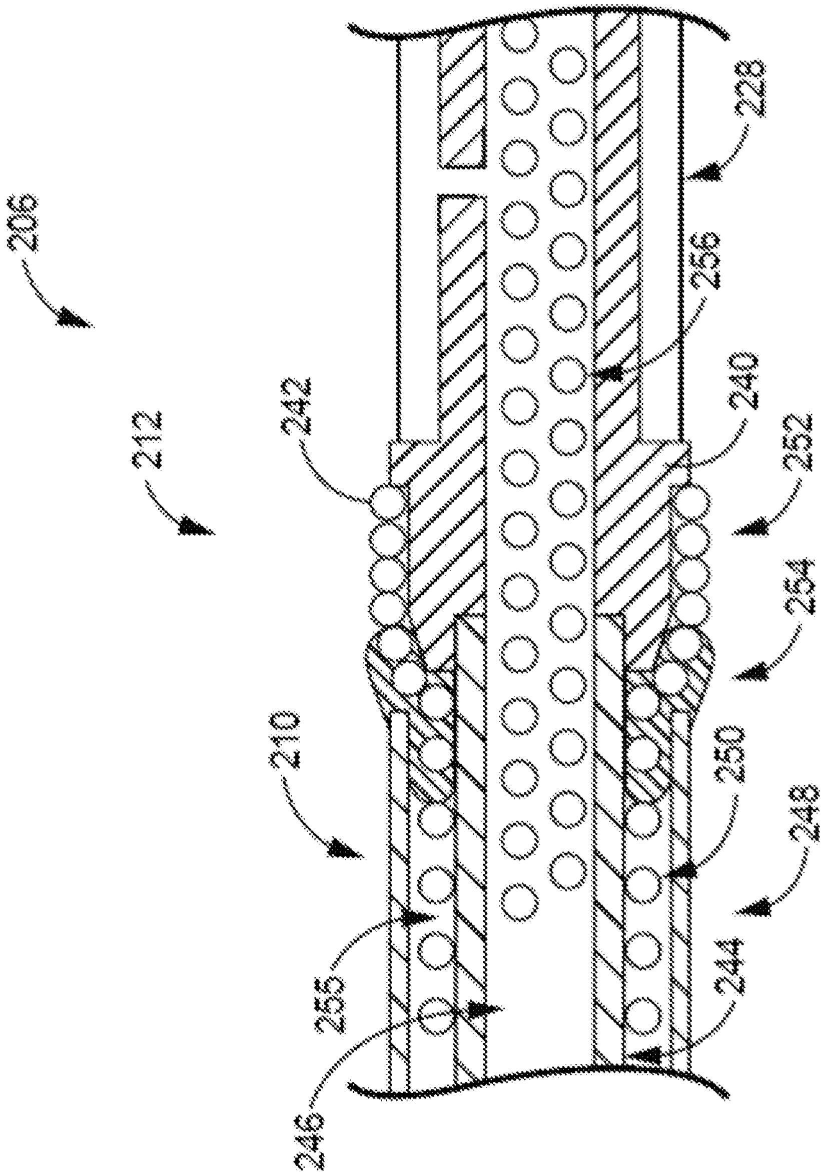
FIG. 2 is a conceptual diagram illustrating a distal portion of an example implantable medical lead in accordance with techniques of this disclosure.

FIG. 2 is a conceptual diagram of an example configuration of a distal portion 212 of a lead 206. Lead 206 may be substantially similar to lead 206 of FIG. 1, except for any differences described herein. As shown in FIG. 2, lead 206 includes a lead body 210, a sleeve 240, a balloon 228 mechanically supported by sleeve 240, and an uninsulated conductor coil 242 ("coil 242").

Lead body 210 may include an inner insulation layer 244 and an outer insulation layer 248. Inner insulation layer 244 and outer insulation layer 248 may be formed from a material that resists conduction of electrical charge. Additionally, inner insulation layer 244 and outer insulation 248 may be configured to seal lead body 210 to prevent infiltration of fluids into lead body 210. In some examples, inner insulation layer 244 and outer insulation layer 248 may be tubular.

Coil 242 may be electrically connected to IMD 108, e.g., via a proximal connector of the lead. Coil 242 may be uninsulated along the entire length of coil 242 (e.g., from a proximal end of coil 242 to a distal end of coil 242). Coil 242 may be formed from any conductive material, such as, but not limited to, MP35N, stainless steel (e.g., Biodur® 108), etc. Coil 242 may include a first portion 250 positioned between inner insulation layer 244 and outer insulation layer 248. First portion 250 may have a first inner diameter sized to enable inner insulation layer 244 (and any components positioned within inner insulation layer lumen 246) to be positioned within first portion 250 of coil 242. For example, the first inner diameter may be slightly larger than the outer diameter of inner insulation layer 244. First portion 250 may have a first winding pitch (e.g., coil pitch, coil span, etc.). As used herein, winding pitch refers to the distance between the two adjacent windings of a coil, such as coil 242.

Coil 242 may further include a second portion 252 extending distally (e.g., in the direction indicated by the arrow 'D' shown in FIG. 2) from outer insulation layer 248. For example, as shown in FIG. 2, a gap may exist between outer insulation layer 248 and sleeve 240 such that coil 242 may extend distally beyond the distal end of outer insulation layer 248. In some examples, coil 242 may be bonded to inner insulation layer 244 and outer insulation layer 248 with an adhesive 254. Adhesive 254 may be electrically insulating and seal the gap (e.g., to prevent infiltration of fluids into lead body 210) between outer insulation layer 248 and sleeve 240.

Second portion 252 may have a second inner diameter sized to at least partially receive sleeve 240 mechanically supported by lead body 210 (e.g., at the distal end of lead body 210). The second inner diameter may be greater than the first inner diameter. For example, the first inner diameter of first portion 250 may flare out such that the second inner diameter of second portion 252 is greater than the first inner diameter. Additionally, in some examples, second portion 252 may have a second winding pitch different from the first winding pitch.

An outer surface of second portion 252 may be exposed (e.g., to tissue of a patient). As such, outer insulation layer 248 may insulate (e.g., cover, surround, encapsulate, etc.) first portion 250 but not second portion 252 of coil 242. In some examples, the outer surface of second portion 252 may be at least partially coated with an electrically conductive material with gold, platinum, etc. For instance, the outer surface of second portion 252 may be electroplated. Because coil 242 may be electrically connected to circuitry 224 of IMD 208, second portion 252 may operate as an electrode (e.g., a proximal electrode of lead 206) by providing stimulation and sensing electrical signals (e.g., of heart 104).

In some examples, the second winding pitch of second portion 252 may be smaller than the first winding pitch of first portion 250 such that the surface area of second portion 252, e.g., exposed to tissue of patient 104 is greater, potentially increasing transmission of electrical energy to the tissue and in turn improving patient outcomes. Conversely, the first winding pitch of first portion 250 may be greater than the second winding pitch of second portion 252 such that first portion 250 is more flexible, which may aid navigation of lead 206 during an implantation procedure.

Coil 242 may define a coil lumen 255. For example, first portion 250 having the first inner diameter may define a first portion of coil lumen 255, and second portion 252 having the second inner diameter may define a second portion of coil lumen 255. At least a portion of inner insulation layer 244 may be positioned within coil lumen 255.

In some examples, lead 206 may further include an inner conductor coil 256 ("inner coil 256"). Inner conductor coil 256 may be electrically connected to a distal electrode and IMD 208. Inner coil 256 may be at least partially uninsulated along the length of inner coil 256 (e.g., from a proximal end of inner coil 256 to a distal end of coil inner 256). Inner coil 256 may be formed from any conductive material, such as, but not limited to, MP35N, stainless steel, etc. Inner coil 256 may be positioned within inner insulation layer lumen 246. Inner coil 256 may be electrically connected to an electrode mechanically supported by lead 206. For instance, inner coil 256 may be electrically connected to a distal electrode (e.g., fixation mechanism 122) mechanically supported by sleeve 240. Inner coil 256 may define an inner lumen, which may accommodate a stylet, a guidewire, etc.

Figure 3A:
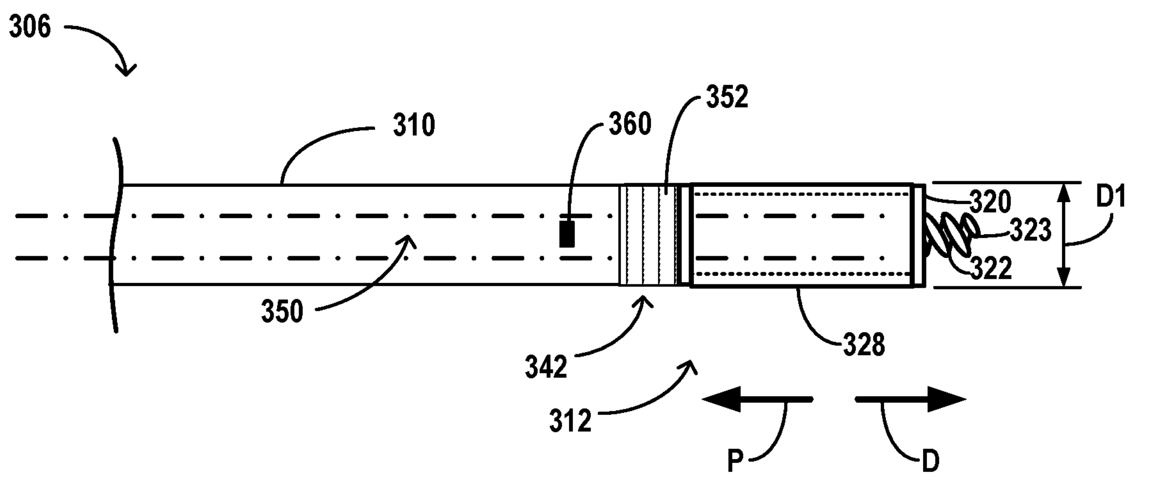
FIGS. 3A and 3B are conceptual diagrams of an example implantable medical lead with a balloon in accordance with techniques of this disclosure.
Figure 3B:
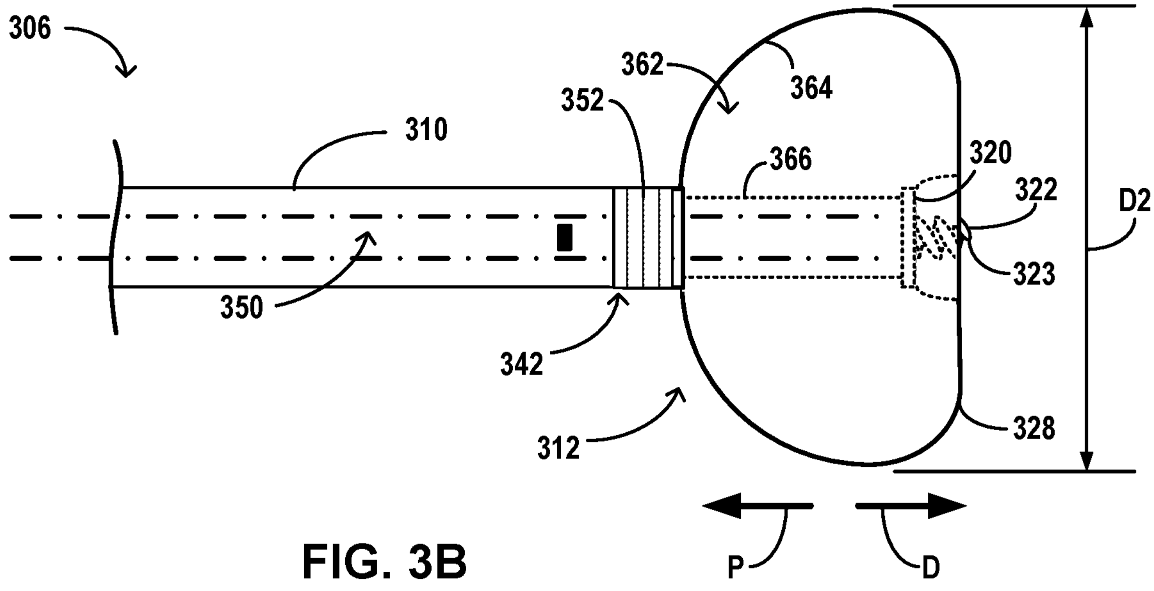

FIGS. 3A-3B are conceptual diagrams of an example lead 306. Lead 306 may be substantially similar to lead 106 of FIG. 1 and/or lead 206 of FIG. 2, except for any differences described herein. For example, lead 306 may include a coil 342 having an exposed second portion 352. Second portion 352 of coil 342 may operate as an electrode, such as a proximal electrode, of lead 306. Additionally, lead 306 may include a balloon 328 located at a lead body distal portion 312. In the example of FIG. 3A, system 300 may be in a configuration which may be utilized to deliver a lead body 310 to vasculature or other areas within patient 104 enroute to positioning lead body distal portion 312 in the vicinity of a target site, such as target site 114, 116. As shown in FIG. 3A, an inflation lumen 350 may extend to balloon 328, such that balloon 328 and inflation lumen 350 are in fluid communication.

Balloon 328 may be affixed to lead body distal portion 312. A fixation member 322 may extend distal (e.g., in the distal direction D) to a lead distal end 320 of lead body distal portion 312. FIG. 3A illustrates system 300 with balloon 328 in the deflated configuration. Fixation member 322 may mechanically support a distal electrode 323 configured to electrically communicate with tissue when positioned in the vicinity of a target site within patient 104, such as target site 114, 116.

In some examples, lead body 310 is positioned within a sheath lumen of a sheath. The sheath may be, for example, an introducer sheath, such an introducer sheath configured to provide access to a jugular, innominate, and/or subclavian vein. In some examples, the sheath is a delivery catheter. The sheath may include an inner wall defining the sheath lumen and further includes a sheath opening to the sheath lumen. System 300 may be configured to translate through the sheath lumen to pass through the sheath opening when balloon 328 is in the deflated configuration.

In any case, balloon 328 may be expanded enroute to positioning lead body distal portion 312 in the vicinity of a target site within patient 104. FIG. 3A illustrates balloon 328 in the deflated configuration and defining a maximum initial dimension D1 (e.g., an inner diameter). System 300 may define maximum initial dimension D1, for example, to allow lead body 310 to translate through a sheath lumen and sheath opening. In examples, lead body 310 includes a marker 360 (e.g., proximal to balloon 328) configured to indicate that balloon 328 is distal to a sheath opening, such that balloon 328 is free to expand without constraint by a sheath lumen 126. Marker 360 may be configured to configured to be visible on an imaging system, such as a fluoroscope, ultrasound, or other systems configured to provide images of system 300 within patient 104.

FIG. 3B illustrates system 300 with balloon 328 in the inflated configuration. Balloon 328 may define an interior volume 362 configured to contain an inflating medium (e.g., air, saline, or another inflating medium) to cause balloon 328 to transition from the deflated configuration of FIG. 3A to the inflated configuration depicted in FIG. 3B. In examples, interior volume 362 is bound at least in part by an inner surface 364 of balloon 328 "(balloon inner surface 364") and an exterior surface 366 of lead body distal portion 312 ("distal exterior surface 366"). A lead body 610 may define an inflation lumen 350 configured to provide the inflating medium to interior volume 362. For instance, inflation lumen 350 may extend to interior volume 362, such that balloon 328 and interior volume 362 are in fluid communication.

In the inflated configuration, balloon 328 may define a maximum expanded dimension D2 (e.g., an inner diameter). The maximum expanded dimension D2 of the inflated configuration is greater than the maximum initial dimension D1 of the deflated configuration. In the inflated configuration, balloon 328 extends distal to a lead distal end 320, with a portion of a fixation member 322 extending distal to balloon 328. Balloon 328 may substantially form a bumper circumferentially around fixation member 322. In examples, balloon 328 defines a substantially toroidal shape surrounding lead body distal portion 312 and lead distal end 320 when balloon 328 is in the inflated condition. Balloon 328 may be configured such that lead body distal portion 312 extends at least partially within a hole defined by the substantially toroidal shape. In examples, fixation member 322 is configured to extend at least partially through the hole defined by the substantially toroidal shape.

Figure 4:
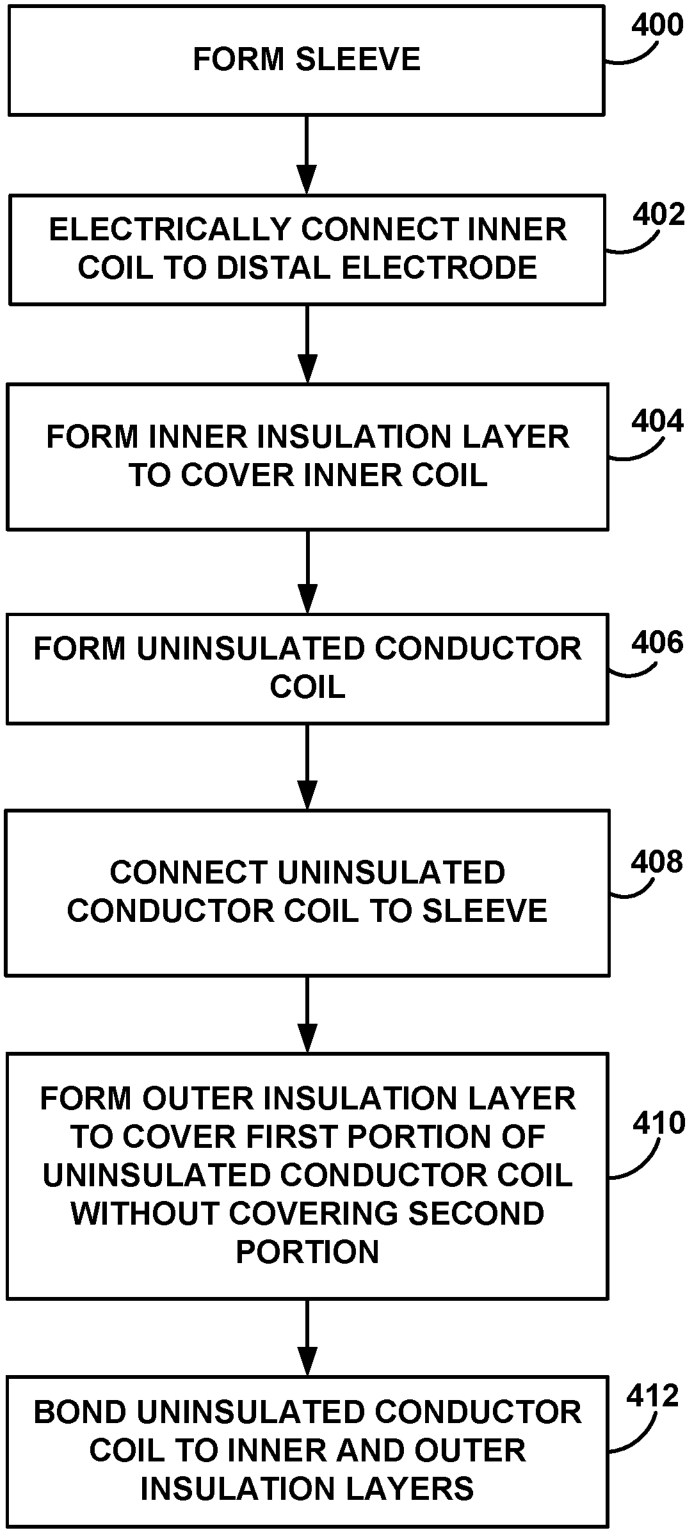
FIG. 4 is a flow diagram of an example technique for manufacturing an example implantable medical lead in accordance with techniques of this disclosure.

FIG. 4 is a flow diagram of an example technique for manufacturing an example implantable medical lead in accordance with techniques of this disclosure. Although FIG. 4 is discussed primarily in the context of lead 206 of FIG. 2, it should be understood that the method of FIG. 4 may be applied to other examples of systems as described herein.

A method of manufacturing lead 206 may include forming sleeve 240 (400). In some examples, sleeve 240 may include balloon 228 and a distal electrode, such as fixation mechanism 122, which may be a helix. In such examples, inner coil 256 may be electrically connected to fixation mechanism 122 (402).

Inner insulation layer 244 may be formed such that inner insulation layer 244 covers inner coil 256, thus insulating inner coil 256 (404). In some examples, inner insulation layer 244 may cover inner coil 256 from a proximal end to a distal end of inner coil 256.

Coil 242 may be formed (406). Coil 242 may be formed to include first portion 250 having a first inner diameter and a first winding pitch. Coil 242 may further be formed to include second portion 252 having a second inner diameter and a second winding pitch. During formation of coil 242, the first inner diameter of first portion 250 may be increased (e.g., flared out) such that the second inner diameter of second portion 252 is greater than the first inner diameter. Additionally, in some examples, second portion 252 may have a second winding pitch different from the first winding pitch. For instance, the second winding pitch may be decreased (e.g., to increase the surface area of second portion 252).

Second portion 252 may be connected to sleeve 240 (408). Outer insulation layer 248 may be formed such that outer insulation layer 248 covers first portion 250 without covering second portion 252 (410). In this way, second portion 252 may be exposed and operate as an electrode, such as a proximal electrode. In some examples, coil 242 may be bonded to inner insulation layer 244 and outer insulation layer 248 with adhesive 254 (412). Adhesive 254 may be electrically insulating and seal the gap between outer insulation layer 248 and sleeve 240.

In some examples, the order of steps of the method of FIG. 4 can be rearranged without impacting the finished product.

Various aspects of the disclosure have been described. These and other aspects are within the scope of the following claims.

What is claimed is:

1. An implantable medical lead comprising:
a lead body extending from a proximal end to a distal end, the lead body comprising:
an inner insulation layer defining an inner insulation layer lumen; and
an outer insulation layer;
a sleeve mechanically supported by the lead body at the distal end of the lead body; and
an uninsulated conductor coil electrically connected to an implantable medical device, the uninsulated conductor coil comprising:
a first portion having a first inner diameter, wherein the first portion is positioned between the inner insulation layer and the outer insulation layer; and
a second portion extending distally from the outer insulation layer, the second portion having a second inner diameter sized to receive the sleeve, wherein the second inner diameter is greater than the first inner diameter, wherein an outer surface of the second portion is exposed, and wherein the uninsulated conductor coil terminates at a distal end of the second portion of the uninsulated conductor coil,
wherein the sleeve extends distally from the distal end of the second portion of the uninsulated conductor coil.

2. The implantable medical lead of claim 1, wherein the uninsulated conductor coil defines a coil lumen, and wherein at least a portion of the inner insulation layer is positioned within the coil lumen.

3. The implantable medical lead of claim 1, further comprising an inner conductor coil positioned within the inner insulation layer lumen, wherein the inner conductor coil is electrically connected to an electrode mechanically supported by the sleeve.

4. The implantable medical lead of claim 1, wherein the uninsulated conductor coil is bonded to the inner insulation layer and the outer insulation layer with an adhesive, wherein the adhesive is electrically insulating, and wherein the adhesive seals a gap between the outer insulation layer and the sleeve.

5. The implantable medical lead of claim 1, further comprising a balloon mechanically supported by the sleeve, wherein the balloon is distal to the distal end of the second portion of the uninsulated conductor coil, and wherein an inner volume of the balloon is bounded by an inner surface of the balloon and an exterior surface of the sleeve.

6. The implantable medical lead of claim 1, wherein the outer surface of the second portion is coated with a conductive material.

7. The implantable medical lead of claim 6, wherein the outer surface of the second portion is electroplated.

8. The implantable medical lead of claim 1, wherein the first portion of the uninsulated conductor coil defines a first winding pitch, and wherein the second portion of the uninsulated conductor coil defines a second winding pitch, the second winding pitch being less than the first winding pitch.

9. A system comprising:
an implantable medical device;
an implantable medical lead comprising:
a lead body extending from a proximal end to a distal end, the lead body comprising:
an inner insulation layer defining an inner insulation layer lumen; and an outer insulation layer;

a sleeve mechanically supported by the lead body at the distal end of the lead body; and an uninsulated conductor coil electrically connected to the implantable medical device, the uninsulated conductor coil comprising:

a first portion having a first inner diameter, wherein the first portion is positioned between the inner insulation layer and the outer insulation layer; and a second portion extending distally from the outer insulation layer, the second portion having a second inner diameter sized to receive the sleeve, wherein the uninsulated conductor coil terminates at a distal end of the second portion of the uninsulated conductor coil, and wherein the sleeve extends distally from the distal end of the second portion of the uninsulated conductor coil.

10. The system of claim 9, wherein the uninsulated conductor coil defines a coil lumen, and wherein at least a portion of the inner insulation layer is positioned within the coil lumen.

11. The system of claim 9, further comprising an inner conductor coil positioned within the inner insulation layer lumen, and wherein the inner conductor coil is electrically connected to an electrode mechanically supported by the sleeve.

12. The system of claim 9, wherein the uninsulated conductor coil is bonded to the inner insulation layer and the outer insulation layer with an adhesive, wherein the adhesive is electrically insulating, and wherein the adhesive seals a gap between the outer insulation layer and the sleeve.

13. The system of claim 9, further comprising a balloon mechanically supported by the sleeve, wherein the balloon is distal to the distal end of the second portion of the uninsulated conductor coil, and wherein an inner volume of the balloon is bounded by an inner surface of the balloon and an exterior surface of the sleeve.

14. The system of claim 9, wherein the outer surface of the second portion is coated with a conductive material.

15. The system of claim 14, wherein the outer surface of the second portion is electroplated.

16. The system of claim 9, wherein the first portion of the uninsulated conductor coil defines a first winding pitch, and wherein the second portion of the uninsulated conductor coil defines a second winding pitch, the second winding pitch being less than the first winding pitch.

17. A method of manufacturing an implantable medical lead, the method comprising:

forming a sleeve of the implantable medical lead, wherein the sleeve comprises a distal electrode;

electrically connecting an inner conductor coil to the distal electrode;

forming an inner insulation layer that covers the inner coil;

forming an uninsulated conductor coil defining a coil lumen, wherein the uninsulated conductor coil comprises:

a first portion having a first inner diameter; and a second portion having a second inner diameter sized to receive the sleeve, wherein the second inner diameter is greater than the first inner diameter, wherein the uninsulated conductor coil terminates at a distal end of the second portion of the uninsulated conductor coil, wherein when the sleeve is received within the second portion, the sleeve extends distally from the distal end of the second portion;

positioning at least a part of the inner insulation layer within the coil lumen;

connecting the second portion to the sleeve; and forming an outer insulation layer that covers the first portion of the uninsulated conductor coil without covering the second portion of the uninsulated conductor coil such that the second portion remains exposed.

18. The method of claim 17, wherein the sleeve further comprises a balloon, wherein when the sleeve is received within the second portion of the uninsulated conductor coil, the balloon is distal to the distal end of the second portion.

19. The method of claim 17, wherein forming the uninsulated conductor coil comprises:

forming the first portion of the uninsulated conductor coil to have a first winding pitch; and forming the second portion of the uninsulated conductor coil to have a second winding pitch, wherein the second winding pitch is less than the first winding pitch.

20. The method of claim 17, further comprising disposing an adhesive around the uninsulated conductor coil between the inner insulation layer and the outer insulation layer, wherein the adhesive is electrically insulating, and wherein the adhesive seals a gap between the outer insulation layer and the sleeve.

* * * * *